United States Patent [19]

Walker

[11] Patent Number: 4,977,181
[45] Date of Patent: Dec. 11, 1990

[54] TROMETHAMINE SALT OF 1-METHYL-BETA-OXO-ALPHA-(PHENYL-CARBAMOYL)-2-PYRROLEPROPIONI-TRILE

[75] Inventor: Gordon N. Walker, Morristown, N.J.

[73] Assignee: Ciba-Geigy Corporation, Ardsley, N.Y.

[21] Appl. No.: 424,297

[22] PCT Filed: Dec. 18, 1987

[86] PCT No.: PCT/US87/03413
§ 371 Date: Aug. 4, 1989
§ 102(e) Date: Aug. 4, 1989

[87] PCT Pub. No.: WO89/05798
PCT Pub. Date: Jun. 29, 1989

[51] Int. Cl.$^5$ .................. C07D 207/337; A61K 31/40
[52] U.S. Cl. ..................................... 514/423; 514/427; 548/530; 548/561
[58] Field of Search ................. 548/561, 530; 514/423, 514/427

[56] References Cited

U.S. PATENT DOCUMENTS

| | | | |
|---|---|---|---|
| 3,880,883 | 4/1975 | Caton | 424/317 |
| 4,089,969 | 5/1978 | Muchowski et al. | 574/416 |
| 4,256,759 | 3/1981 | Walker | 548/248 |
| 4,518,608 | 5/1985 | Kahan | 514/420 |
| 4,644,010 | 2/1987 | Walker | 548/540 |
| 4,704,405 | 11/1987 | O'Neill et al. | 514/568 |

FOREIGN PATENT DOCUMENTS 2211187  6/1989  United Kingdom ................ 548/561

Primary Examiner—Mark L. Berch
Attorney, Agent, or Firm—Norbert Gruenfeld

[57] ABSTRACT

The present invention is concerned with the novel pharmaceutically acceptable tromethamine salt of 1-methyl-beta-oxo-alpha-(phenylcarbamoyl)-2-pyrrolepropionitrile of the formula II

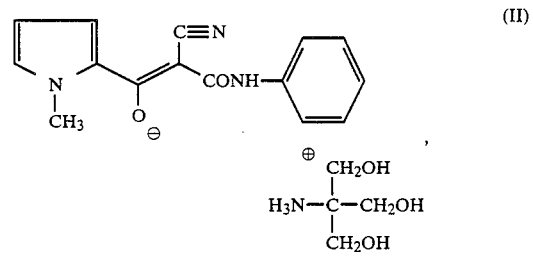

pharmaceutical compositions comprising said salt and a method of treating inflammatory and arthritic conditions in mammals by administering said salt to mammals in need of such treatment.

6 Claims, No Drawings

TROMETHAMINE SALT OF 1-METHYL-BETA-OXO-ALPHA-(PHENYLCARBAMOYL)-2-PYRROLEPROPIONITRILE

BACKGROUND OF THE INVENTION

U.S. Pat. No. 4,256,759 discloses 1-methyl-beta-oxo-alpha-phenylcarbamoyl-2-pyrrolepropionitrile of formula I,

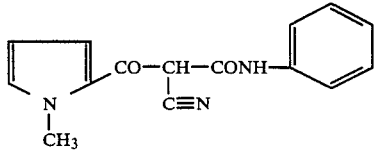

The compound of formula I is acidic and may exist in a tautomeric enolic form represented by formula Ia

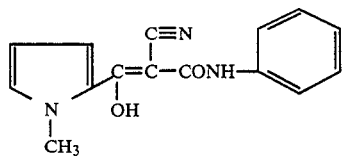

Salts mentioned in U.S. Pat. No. 4,256,759 for the class of compounds are salts with pharmaceutically acceptable bases, such as alkali metal, alkaline earth metal, copper or zinc hydroxides; ammonia, mono-, di- or tri-lower (alkyl or hydroxyalkyl)-amines, alkyleneimines or alkylenediamines, e.g. sodium, potassium, magnesium, ammonium, mono-, di- or tri-(methyl, ethyl or hydroxy-ethyl)-ammonium, pyrrolidinium, ethylenediammonium or morpholinium salts; or various hydrates thereof.

Salts specifically disclosed for the compound of formula I are the sodium salt, potassium salt, calcium salt and tris-hydroxyethyl-ammonium (triethanolamine) salt. The sodium, potassium and calcium salts are not crystalline.

Tromethamine is the primary amine tris-(hydroxymethyl)-aminomethane, also named 2-amino-2-(hydroxy-methyl)-1,3-propanediol, and described in Merck Index, Tenth Edition page 1395.

The tertiary amine triethanolamine has been converted chemically in the laboratory to N-nitrosodiethanolamine which has been implicated as a potential carcinogen. Some concerns have been expressed about triethanolamine salts as pharmaceuticals based on the speculation that triethanolamine might somehow be converted metabolically in mammals to N-nitrosodiethanolamine.

On the other hand, the primary amine tromethamine is not known to be chemically convertible to any N-nitroso derivative.

SUMMARY OF THE INVENTION

The present invention is concerned with the novel pharmaceutically acceptable tromethamine salt of 1-methylbeta-oxo-alpha-(phenylcarbamoyl)-2-pyrrole-propionitrile, pharmaceutical compositions comprising said salt and a method of treating inflammatory and arthritic conditions in mammals by administering said salt to mammals in need of such treatment.

DETAILED DESCRIPTION OF THE INVENTION

More specifically the present invention is concerned with the 1:1 salt of 1-methyl-beta-oxo-alpha-(phenylcarbamoyl)-2-pyrrole-propionitrile with tromethamine which can be represented by structural formula II

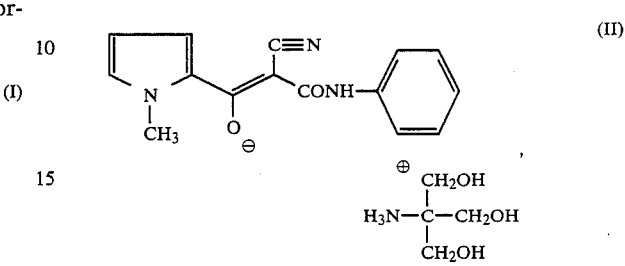

The novel salt of formula II displays antiinflammatory and antiarthritic activity. The salt of formula II also displays biological activity indicative of potential disease modifying effects in arthritis, including inhibition of cartilage matrix degradation as well as enhancement of depressed cell-mediated immunity.

The salt is well tolerated and is essentially free of undesirable side effects at therapeutically effective doses.

In acute toxicity studies in the rat, the salt of the instant invention is observed to be less toxic than the free acid of formula I or the triethanolamine salt thereof. No deaths (0/10 animals) are observed with the tromethamine salt of formula II at a dose of 2.4 millimoles/Kg p.o. (932 mg/Kg p.o.) while a 50% mortality rate is observed with the triethanolamine salt of the compound of formula I at an equimolar dose of 2.4 millimoles/Kg p.o. (1000 mg/Kg p.o.), and a 40% mortality rate is observed at an equimolar dose of 2.4 millimoles/Kg p.o. (641 mg/Kg p.o.) with the free acid of formula I.

In addition, the tromethamine salt of the instant invention is free of concerns relating to any potential metabolic conversion to an N-nitroso derivative.

The foregoing attributes render the compound of the invention particularly useful when administered alone or in combination, to mammals including man, for the treatment of e.g. rheumatoid arthritis and osteoarthritis.

The pharmacological properties, primarily anti-inflammatory, analgesic, antirheumatic, immunopotentiating and antiarthritic activity, can be demonstrated by in-vitro or in-vivo tests, using for the latter advantageously mammals, such as rats, mice, guinea pigs or dogs, as test objects. The compound can be administered to the animals either enterally, preferably orally, parenterally, e.g. subcutaneously or intravenously, or topically, for example, in the form of aqueous solutions or suspensions. The applied dosage may range between about 0.1 and 100 mg/kg/day, preferably between about 1 and 50 mg/kg/day. The tests include the classical in vivo assay methods for said activities, such as the carrageenin paw-edema, adjuvant arthritis tests in rats, and the canine synovitis test.

Concentrations of compound used in in vitro tests range from about $1 \times 10^{-8}M$ to $1 \times 10^{-4}M$, preferably from about $1 \times 10^{-7}M$ to $1 \times 10^{-5}M$. Such tests include the in vitro neutral protease inhibition, described in Arthritis Rheum. 17, 47 (1974), or inhibition of neutrophil chemotaxis, described in Ann. N.Y. Acad. Sci., 256, 177 (1975); or decrease of leukocyte adherence, described in Amer. J. Med. 61, 597 (1976).

The inhibition of the chemotactic activation of neutrophils can be determined in vivo by measuring the inhibition of the accumulation of neutrophils into implanted carrageenin impregnated polyurethane sponges on oral administration of the compound to the rat.

Immunopotentiating effects can be determined in BCG-immunized animals. In vitro, the enhancement of cell-mediated immunity is determined by measuring the increase in chemotaxis of macrophages isolated from BCG-immunized rats. In vivo, such is determined in the BCG-immunized adjuvant arthritic rat by measuring the effect on delayed hypersensitivity reaction essentially as described in Current Therapeutic Research 30, S34 (1981).

The effect on cartilage matrix degradation can be determined in the cartilage-synovium co-culture model of matrix degradation which is carried out as follows:

The proteoglycan matrix of bovine nasal septum cartilage is labeled in vitro by incorporation of $^{35}S$ into glycosaminoglycan. Cartilage slices are incubated overnight in a sulfate-free medium containing $^{35}S$-sodium sulfate. $^{35}S$-Labeled cartilage slices are co-cultured with normal synovium explants in multiwell tissue culture plates. After 4 days incubation a 100 $\mu$l aliquot of medium is counted. Cartilage slices are hydrolyzed and a 100 $\mu$l aliquot of cartilage hydrolysate is counted. The percent $^{35}S$ released into the medium is determined and the percent of inhibition of matrix degradation is calculated.

The inhibition of cartilage matrix degradation can also be determined by measuring the inhibition of the breakdown of cartilage by neutral proteases obtained from human blood leukocytes.

The crystalline tromethamine salt of the present invention is prepared by reacting the compound of formula I advantageously with an equimolar amount or slight excess of tromethamine in the presence of a suitable inert solvent, e.g. an alcoholic or ethereal solvent or mixtures thereof, so as to crystallize the salt from solution. Suitable solvents are for example ethanol, isopropanol, a mixture of tetrahydrofuran and methyl t-butyl ether, or a mixture of ethanol and toluene. The salt formation is generally carried out in the more polar solvent, and the second less polar solvent is added at elevated temperature in an amount sufficient to achieve crystallization of the product.

The starting material of formula I is prepared as described in U.S. Pat. No. 4,256,759.

The tromethamine salt of the invention may be a hydrate or may include other solvents which are used for the crystallization of the product.

The pharmaceutical compositions according to the invention are those suitable for enteral, such as oral or rectal, and parenteral administration, to mammals including man, for the alleviation and treatment of inflammatory/arthritic disorders such as osteoarthritis and rheumatoid arthritis, and of immunologically mediated diseases, comprising an effective amount of the pharmacologically active compound of formula II in combination with one or more pharmaceutically acceptable carriers.

The pharmacologically active salt of the invention is incorporated into pharmaceutical compositions containing an effective amount thereof in conjunction or admixture with excipients suitable for either enteral, parenteral or topical application. Preferred are tablets and gelatin capsules comprising the active ingredient together with (a) diluents, e.g. lactose, dextrose, sucrose, mannitol, sorbitol, cellulose, hydroxypropyl methylcellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatin, tragacanth, methylcellulose, sodium carboxymethylcellulose and/or polyvinylpyrrolidone; if desired (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories or topical lotions are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively and contain about 0.1 to 75%, preferably about 1 to 50%, of the active ingredient.

The invention further relates to a method of treating and ameliorating inflammatory and arthritic disorders, such as rheumatoid arthritis or osteoarthritis, in mammals including man, which comprises administering to a mammal in need thereof an effective amount of the compound of the invention or of a pharmaceutical composition comprising the compound of the invention in combination with one or more pharmaceutically acceptable carriers.

The dosage of active compound administered is dependent on the species of warm-blooded animal (mammal), the body weight, age and individual condition, and on the form of administration.

The unit dosage for a mammal of about 50 to 70 kg may contain between about 100 to 500 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of the product is confirmed by analytical methods, particularly spectroscopic characteristics (e.g. MS, IR, NMR) and elemental analysis.

EXAMPLE 1

A suspension of 10.09 g of 1-methyl-beta-oxo-alpha-(phenylcarbamoyl)-2-pyrrolepropionitrile in 160 ml of tetrahydrofuran is heated to reflux, the resulting solution is cooled to 50°-55°, and treated with 5.22 g of tromethamine. The resulting mixture is stirred at reflux for one half hour, cooled to about 45°-50°, then treated with activated charcoal, stirred until room temperature is reached, and filtered with the aid of Hyflo. The resulting solution is reduced to a volume of about 50 ml; 40 ml of methyl t-butyl ether is slowly added and the mixture is stirred at 15°-20° for two hours. The crystalline product is collected, washed with a 1:1 mixture of tetrahydrofuran and methyl t-butyl ether, dried at 80° under vacuum overnight to yield 1-methyl-beta-oxo-alpha-(phenylcarbamoyl)-2-pyrrolepropionitrile (1:1) tromethamine salt, m.p. 163°-165°.

EXAMPLE 2

A suspension of 13.36 g of 1-methyl-beta-oxo-alpha-(phenylcarbamoyl)-2-pyrrolepropionitrile and 6.06 g of tromethamine in 100 ml of ethanol is heated to reflux for about one half hour, the solution is allowed to cool to about room temperature, treated with activated charcoal, filtered and reduced to a volume of about 45 ml at a temperature below 60°. The solution is heated to about 50°-55°, 100 ml of toluene is slowly added over a period of about one half hour with stirring and the resulting mixture is slowly cooled to about 15° over a period of one hour and stirred at 15° about 1 hour. The resulting crystalline product is collected by filtration, washed with toluene and dried at 70°-80° under low vacuum for 24 hours to yield 1-methyl-beta-oxo-alpha-(phenylcarbamoyl)-2-pyrrolepropionitrile tromethamine salt of Example 1. Second crop can be obtained by evaporating mother liquor to dryness and crystallizing more product from ethanol: toluene (1:2) as described above.

EXAMPLE 3

To a suspension of 13.85 g of 1-methyl-beta-oxo-alpha-(phenylcarbamoyl)-2-pyrrolepropionitrile in 350 ml of ethanol is added 6.1 g of tromethamine. The suspension is heated until solution is obtained and the volume is reduced to about 75 ml. The solution is cooled to crystallize the product, the salt is collected, washed with ethanol/ether and dried to yield 1-methyl-beta oxo-alpha-(phenylcarbamoyl)-2-pyrrolepropionitrile tromethamine (1:1) salt of example 1.

EXAMPLE 4

Preparation of 10,000 tablets each containing 250 mg of the active ingredient:

| | |
|---|---|
| 1-Methyl-beta-oxo-alpha-(phenylcarbamoyl)-2-pyrrolepropionitrile tromethamine | 2,500.0 g |
| Colloidal silica | 20.0 g |
| Microcrystalline cellulose | 465.0 g |
| Hydroxypropyl methylcellulose | 160.0 g |
| Cross-linked polyvinylpyrrolidone | 200.0 g |
| Magnesium stearate | 35.0 g |
| Purified water | q.s. |

The drug substance, the silica and the hydroxypropyl methylcellulose are mixed in a suitable mixer for about 20 minutes. The mixture is granulated with a sufficient amount of water. The wet granules are broken up in a mill, passed through a #5 screen, dried at 35° for 6 hours, then further broken up in a mill and passed through a #2 screen. The resulting granules, the cellulose and the polyvinylpyrrolidone are then mixed together in a suitable mixer for about 15 minutes, the magnesium stearate (first passed through a #30 screen) is added, and is mixed with the above for about 5 minutes. The resulting granulation is then compressed into tablets. The tablets may then be film-coated, if so desired.

EXAMPLE 5

Acute Toxicity Study

A single equimolar dose of each compound is administered orally by gavage as a 3% corn starch suspension to 5 female and 5 male Sprague-Dawley rats. The animals are there observed for 15 days.

The comparative incidence of mortality for the free acid of formula I, the triethanolamine salt thereof and the tromethamine salt of formula II are as follows:

(a) for 1-methyl-beta-oxo-alpha-(phenylcarbamoyl)-2-propionitrile (I, mol. wt.: 267.28)

| Dose | | Mortality | |
|---|---|---|---|
| Millimoles/Kg | Mg/Kg | Male | Female |
| 1.2 | 321 | 0/5 | 0/5 |
| 2.4 | 641 | 2/5 | 2/5 |
| 3.6 | 962 | 4/5 | 4/5 |

(b) for the triethanolamine salt of 1-methyl-beta-oxo-alpha-(phenylcarbamoyl)-2-propionitrile (mol. wt.: 416.49).

| Dose | | Mortality | |
|---|---|---|---|
| Millimoles/Kg | Mg/Kg | Male | Female |
| 1.2 | 500 | 0/5 | 0/5 |
| 2.4 | 1000 | 2/5 | 3/5 |
| 3.6 | 1500 | 5/5 | 5/5 |

(c) for the tromethamine salt of 1-methyl-beta-oxo-alpha-(phenylcarbamoyl)-2-propionitrile (II, mol. wt.: 388.41).

| Dose | | Mortality | |
|---|---|---|---|
| Millimoles/Kg | Mg/Kg | Male | Female |
| 1.2 | 466 | 0/5 | 0/5 |
| 2.4 | 932 | 0/5 | 0/5 |
| 3.6 | 1398 | 5/5 | 5/5 |

What is claimed is:

1. The tromethamine salt of 1-methyl-beta-oxo-alpha-(phenylcarbamoyl)-2-pyrrolepropionitrile.

2. An antiinflammatory or antiarthritic pharmaceutical composition comprising an effective amount of the compound of claim 1 in combination with one or more pharmaceutically acceptable carriers.

3. A method of treating inflammatory or arthritic conditions in mammals which comprises administering to a mammal in need thereof an effective amount of the compound of claim 1 or of a pharmaceutical composition comprising said compound.

4. A method according to claim 3 of treating rheumatoid arthritis.

5. A method according to claim 3 of treating osteoarthritis.

6. A method of inhibiting neutrophil chemotaxis in mammals which comprises administering to a mammal in need thereof an effective amount of the compound of claim 1 or of a pharmaceutical composition comprising said compound.

* * * * *